United States Patent [19]
Teicher

[11] Patent Number: 5,833,974
[45] Date of Patent: Nov. 10, 1998

[54] METHOD OF ENHANCING THE EFFECTIVE LIFE OF OXYGEN-DELIVERY AGENTS

[76] Inventor: Beverly A. Teicher, 135 Hunting Rd., Needham, Mass. 02194

[21] Appl. No.: 632,795

[22] Filed: Apr. 17, 1996

[51] Int. Cl.⁶ .......................... A61M 37/00; A61K 38/42
[52] U.S. Cl. ......................... 424/78.26; 604/23; 604/26
[58] Field of Search ................... 604/23, 26; 424/78.08

[56] References Cited

U.S. PATENT DOCUMENTS

| | | | |
|---|---|---|---|
| 1,474,205 | 6/1923 | Yuhas et al. | 514/34 |
| 5,049,388 | 9/1991 | Knight et al. | 424/450 |
| 5,295,944 | 3/1994 | Teicher et al. | 600/1 |
| 5,386,014 | 1/1995 | Nho et al. | 530/585 |

OTHER PUBLICATIONS

B. Teicher et al., J. Cancer Res. Clin, Oncol., 118(2):123–128(1992).
B. Teicher et al., In Vivo, 9(1):11–18(1995).
S. Rockwell, Artificial Cells Blood Substitutes and Immobilization Biotechnology, 22(4):1097–1108(1994).
J. Tanaka et al., Anticancer Res., 12(3):1029–1033(1992).
M. Robinson et al., Artificial Cells Blood Substitutes and Immobilization Biotechnology, 23(3):431–438(1995).

*Primary Examiner*—Peter F. Kulkosky
*Attorney, Agent, or Firm*—David G. Conlin; Ronald I. Eisenstein; Dike, Bronstein, Roberts & Cushman, LLP

[57] ABSTRACT

A method of increasing the effective life of oxygen-delivery agents is described. The method involves administering an oxygen-enriched atmosphere to a subject that has received the oxygen-delivery agent at a predetermined time.

14 Claims, 10 Drawing Sheets

METHOD OF ENHANCING THE EFFECTIVE LIFE OF OXYGEN-DELIVERY AGENTS

The present invention is directed to enhancing the effective life of oxygen-delivery agents, particularly those used in anti-tumor therapies involving hemoglobin-polymer conjugate.

Tumors, such as solid tumors, have a high percentage of hypoxic cells. These regions of hypoxia have been shown to occur in many solid tumor model systems [Gullino, P. M., et al., *Adv. Exp. Med. Biol.* 75:521–536 (1975); Hasegawa, T., et al., *Int. J. Radiat. Oncol. Biol. Phys.* 13:569–574 (1987); Jain, R., et al., *Cancer Res.* 48:2641–2658 (1988); Siemann, D., et al., *Br. J. Cancer* 58:296–300 (1988); Song, C., et al., *Cancer Res.* 47:442–446 (1987); Vaupel, P., et al., *Cancer Res.* 47:3496–3503 (1987); Vaupel., P., et al., *Cancer Res.* 41:2008–2013 (1981)] and in human solid tumors [Vaupel, P., et al. *Cancer Res.* 49:6449–6465 (1989)] by several different methods. These regions occur because oxygen is rapidly metabolized by cells and consequently, has a limited diffusion distance from blood vessels [Gatenby, R. A., et al., *Init. J. Radiat. Oncol. Biol. Phys.* 14:831–838 (1988)].

Tumors such as solid tumors are aberrant tissues comprising stroma and malignant cells. Among the properties which distinguish normal tissue from solid tumors are physiological characteristics related to the disregulated proliferation of neoplastic and normal cells that comprise the tumor mass. While signals for vascular growth are present in solid tumors, the growth of such blood vessels in the tumor is irregular and the vasculature is often poorly formed and inadequate, lacking vasoresponsive elements. Thus, the resultant tumors often exhibit highly heterogenous regions with respect to properties such as oxygen tension distributions, pH, glucose delivery and utilization, etc. [Dewhirst, M. W., et al., Drug Resistance in *Oncology*, 3–24 (1993); Kennedy, K. A., et al., *Biochem. Pharmacol.*, 29:1–8 (1980); Sartorelli, A. C., et al., *Cancer Res.* 48:775–778 (1988); Teicher, B. A., et al., *Cancer Res.* 41:73–81 (1981); Vaupel, P., *Drug Resistance in Oncology*, NY, N.Y.:Marcel-Dekker, 53–85(1993); Vaupel, P., et al., *Cancer Res.* 49:6449–6465 (1989)].

While various anti-neoplastic agents such as radiation and chemotherapy take advantage of the rapid metabolism of the tumor cells in comparison to normal cells, the hypoxic cells are typically protected from the cytotoxic actions, because of their lack of cellular oxygen [Keyes, S. R., et al., *Cancer Res.* 45:3642–3645 (1985); Teicher, B. A., et al., *Cancer Res.* 47:5036–5041 (1987); Teicher, B. A., et al., *Cancer Res.* 47:513–518 (1987); Teicher, B. A., et al., *J. Natl. Cancer Inst.* 75:1129–1133 (1985); Teicher, B. A., et al., *Biomater., Artif. Cells, Immobil. Biotech.* 16:533–546 (1988); Teicher, B. A., et al., *Cancer Res.* 49:4996–5001 (1989)].

It has also been known that anemia can lead to resistance by tumor tissue to radiation therapy [Motram, J. C., et al. *Br. J. Surg.* 194:481–487 (1932)]. After increasing the hematocrit, oxygen delivery to tissues is a compromise between the higher oxygen-carrying capacity afforded by an increased number of red blood cells and the increased viscosity of the blood, which may lead to decreased blood flow. The effect of increased hematocrit is likely to be transient, because adaptation to altered oxygen delivery always occurs; and while it is possible to exploit adaptation to anemia by retransfusing to normal values before irradiation [Hewitt, H. B., et al., *Br. J. Cancer* 25:323–336 (1971); Hill, R. P., et al., Fielden M, Fowler J F and Hendry Scott J H, ed. *The 8th International Congress of Radiation Res.* London (1987)] the therapeutic benefit afforded by that approach was very short-lived in the single doses of radiation and mass tumor [Hirst, D. G., *Int. J. Radiat. Oncol. Biol. Phys.* 180:281–291 (1986); Hirst, D. G., et al., *Int. J. Radiat. Biol.* 46:345–354 (1984)]. It has further been found that cancer patients are typically anemic and such anemia is believed to be an important prognostic factor. Furthermore, increasing hemoglobin levels into the normal range can improve the prognosis and treatment outcome for radiation [Vaupel, P., Strahlenther Onkol. 166:377–386 (1990); Vaupel, P., *Drug Resistance in Oncology*; 53–85; Marcel-Dekker; NY, N.Y. (1993)].

Human progress against substantial medical problems involves recognition and characterization of the problem (diagnosis) and having the tools available to correct the problem (treatment). The importance of oxygen ($O_2$) to the effectiveness of several cancer therapies and the fact that significant regions of reduced oxygen content exist in solid tumor model systems have been recognized for 30 or more years. Laboratory investigators have characterized tumor hypoxia through the study of tumor vasculature, by modeling its effects in various in vitro systems, and by assessing its effects on therapeutic response. Laboratory investigators have explored numerous strategies for overcoming tumor hypoxia as a therapeutic barrier, and some of these have undergone clinical trials. The most straightforward approach to reducing hypoxia would be to supply oxygen to the hypoxic tissue, if possible. However, accomplishing this goal is not that straightforward. Experimental strategies that have been successful in increasing tumor oxygenation have resulted in improved therapeutic response.

Tools are now available to characterize oxygenation/hypoxia in the clinic. The clinical investigations conducted thus far have shown that significant regions of hypoxia exist in solid tumors in patients. The Eppendorf $pO_2$ histograph microelectrode system is now available and allows the evaluation of tissue tumor oxygenation, minimizing tissue compression by the needle electrode [Fleckenstein, W. Berlin:*Blackwell Ueberreuter Wissenchaft* (1990) ; Hockel, M., et al., *Cancer Res.* 51:6098–6102, (1991); Kallinowski, F., et al., *Int. J. Radiat. Oncol. Biol. Phys.* 19:953–961 (1990); Sevick, E. M., et al., *Cancer Res.* 49:3513–3519 (1989); Singbartl, G., et al., *Clinical Oxygen Pressure Measurement*, Berlin: *Blackwell Ueberreuter Wissenschaft*:15–29 (1990); Teicher, B. A., et al., *J. Cancer Res. Clin. Oncol.* 120(10) 593–598 (1994); Teicher, B. A., et al., *Drug Development Res.* 34:231–240 (1995); Teicher, B. A., et al., *Art. Cells, Blood Subs. & Immob. Biotech* 22:827–833 (1994); Teicher, B. A., et al., *J. Cancer Res. Clin. Oncol.* 120:85–90 (1993); Teicher, B. A., et al., *Art. Cells, Blood Subs., & Immob. Biotech* 22(4):1369–1375 (1994); Vaupel, P., et al., *Radiat. Res.* 120:477–493 (1989); Vaupel, P., et al., *Cancer Res.* 51:3316–3322 (1991)]. Investigators at several centers using this computerized $pO_2$ measurement system have been accruing oxygen data in breast tumors, cervix tumors, head and neck tumors, melanoma, brain tumors, soft tissue sarcomas and other tumors as well as normal tissues [Brizel, D. M. et al., *Int. J. Radiat. Oncol. Biol. Phys.* 30(3):635–642: (1994); Brizel, D. J., et al., *Int. J. Radiat. Oncol. Biol. Phys.* 32(4):1121–1125 (1995); Hockel, M., et al., *Cancer Res.* 51:6098–6102 (1991); Lartigau, E., et al., *Cancer* 71:2319–2325 (1993); Lartigau, E., et al., *Radiat. Oncol. Invest.* 1:285–291 (1994); Martin, L., et al., *Radiat. Ther. Oncol.* 27:123–130 (1993); Okunieff, P., et al., *Int. J. Radiat. Oncol. Biol. Phys.* 26:631–636 (1993); Rampling, R., et al., *Int. J. Radiat. Oncol. Biol. Phys.* 29(3):427–431 (1994); Vaupel, P., et al., *Adv. Exp. Med. Bio.* 316:361–371 (1992)].

Frequently, the mean (and median) $pO_2$ values measured in the malignancies were much lower than in the corresponding normal tissues. The percentage of $pO_2$ values $\leq 5$ mmHg was higher in the malignancies than in the corresponding normal tissues. From these published data, it may be concluded that at least half of tumors in the clinic have therapeutically important levels of hypoxia. Of the various strategies developed in the laboratory for reducing (or eliminating) hypoxia in tumors, the intravenous administration of nontoxic oxygen-carrying materials is probably the most generally clinically applicable.

Oxygen is normally delivered to the tissues by the off-loading of $O_2$ bound to the hemoglobin tetramer contained in red blood cells [Chang, T. M. S., *Biomater. Artif. Cells Artif. Organs* 16:1–11 (1988); Chang, T. M. S., *Biomater., Artif. Cells, Immobil. Biotech* 20(2–4):159–179 (1992); Chang T. M. S., *Biomater Artif. Cells, Immobil. Biotech.* 16:11–29 (1988)]. The partial pressure of oxygen and the pH are important factors in the regulation of hemoglobin function in the transport of oxygen. For example, in lungs where the partial pressure of oxygen is high (about 110 mmHg;13 kPa) and the pH is relatively high (pH 7.60), hemoglobin tends to be almost maximally saturated with oxygen (about 96%). In the interior of peripheral tissues, where the oxygen tension is low, (about 50 mmHg; 7 kPa) and the pH is lower (7.20), hemoglobin binds oxygen less strongly and off-loads oxygen to a level of about 65% saturation.

Thus, attempts have been made to provide oxygen delivery agents such as perfluorochemical emulsions and hemoglobin preparations to increase oxygenation. One preferred method has been the use of hemoglobin preparations such as hemoglobin-polymer preparations. For example, hemoglobin was attached to a carrier such as a poly(alkaline oxide) for example, polyethylene glycol (PEG). See, U.S. Pat. No. 5,478,806, which is incorporated herein by reference. Derivation of hemoglobin with carriers such as PEG has been found to enhance anti-tumor therapies, particularly those involving radiation.

However, one of the difficulties with such methods of oxygenation is the relatively short circulating half-life. For example, the circulating half-life of PEG-hemoglobin in rats bearing the 13762 mammary carcinoma is about 20 hours. Thus, typically these compositions are administered just prior to each radiation or chemotherapy dose to be most effective.

It would be desirable if there was a simple method to extend the effective life of these carriers. This would limit the amount of the agent used, frequency of administration, and the consequent treatment-load.

SUMMARY OF THE INVENTION

We have now found that one can increase the effective life of oxygen delivery agents, particularly hemoglobin-carrier conjugates by administering to a subject an oxygen-enhanced atmosphere. The oxygen level need be only slightly above atmospheric levels, for example an atmosphere containing at least: about 25% oxygen, more preferably at least 28% $O_2$, still more preferably, at least about 50% $O_2$, even more preferably at least about 75% $O_2$ and still more preferably at least about 95% $O_2$.

This oxygenation can occur by administering to the subject an oxygen-enriched atmosphere at least about 10 minutes prior to and during the treatment modality, still more preferably one administers the oxygen-enriched atmosphere for at least 15 minutes prior to and during treatment. This is particularly useful when using a treatment such as radiation or chemotherapy, more preferably, radiation.

DETAILED DESCRIPTION OF THE INVENTION

Figure 1A:
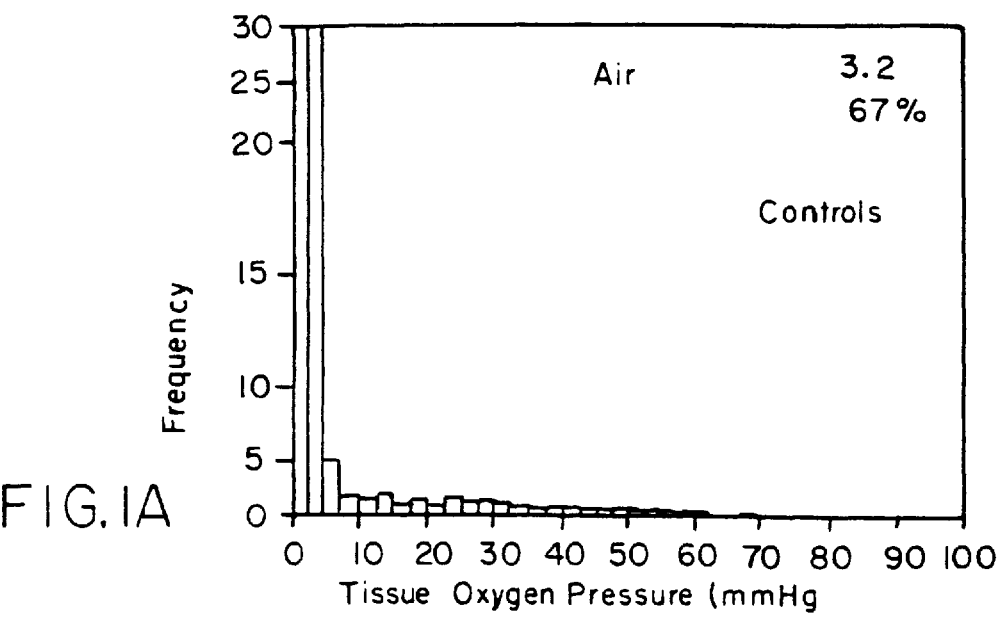
FIGS. 1A–J are histograms showing the oxygen profiles as well as the median $pO_2$ values (top number in each histogram, in mmHg) and the percent of $O_2$ values $\leq 5$ mmHg (bottom number in each histogram) for the rat 13672 mammary carcinoma under normal air breathing (FIG. 1A–1E) and carbogen (95% oxygen/5% carbon dioxide) (FIGS. 1F–1J) breathing conditions, alone (FIGS. 1A, 1F) or after intravenous (iv) administration of the PEG-Hb (2, 4, 6 or 8 ml/kg) (FIGS. 1B and 1G, 1C and 1H, and 1E and 1J, respectively). Approximately 50 measured values were obtained per tumor per condition. Each histogram represents 500–3,000 measured $pO_2$ values.
Figure 1B:
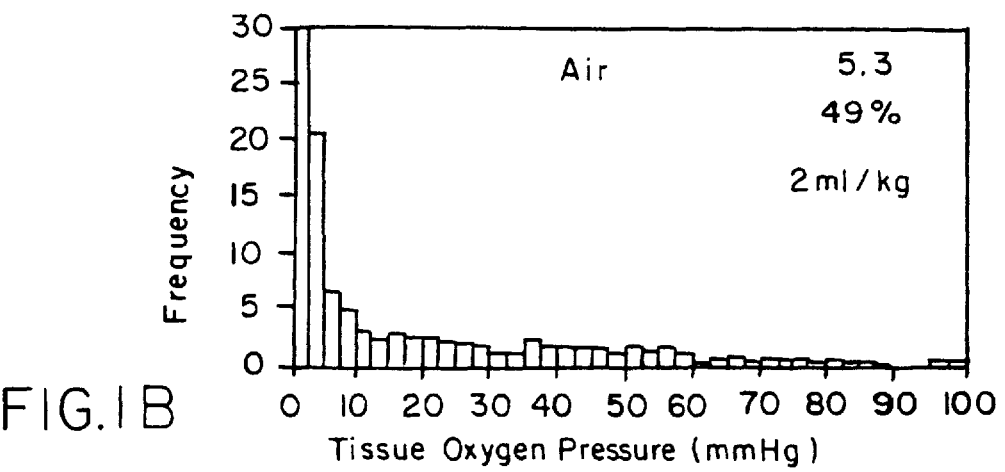
Figure 1C:
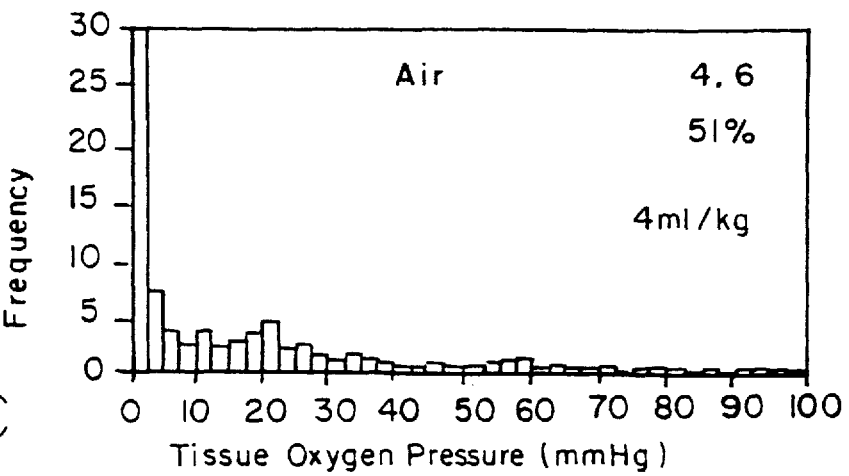
Figure 1D:
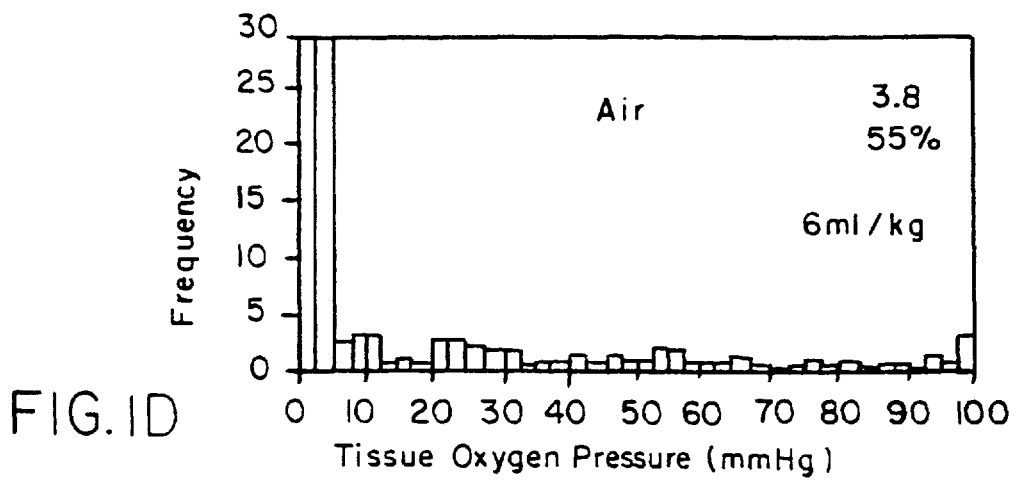
Figure 1E:
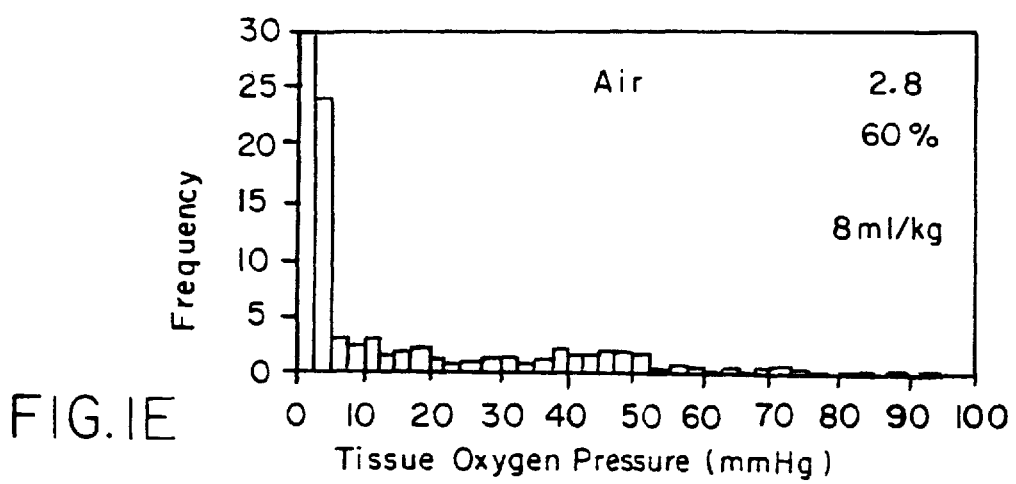
Figure 1F:
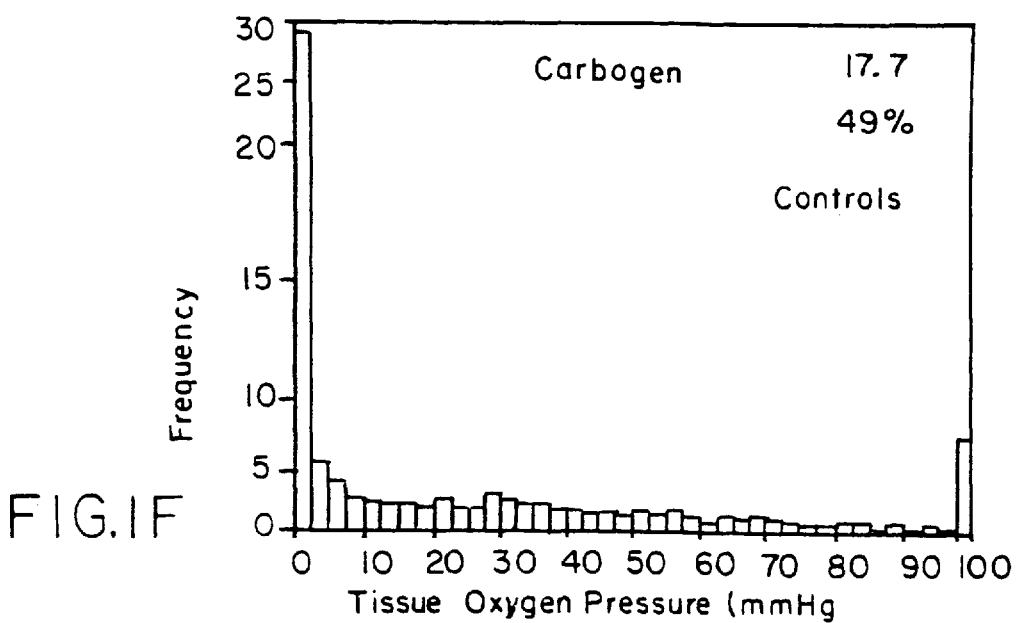
Figure 1G:
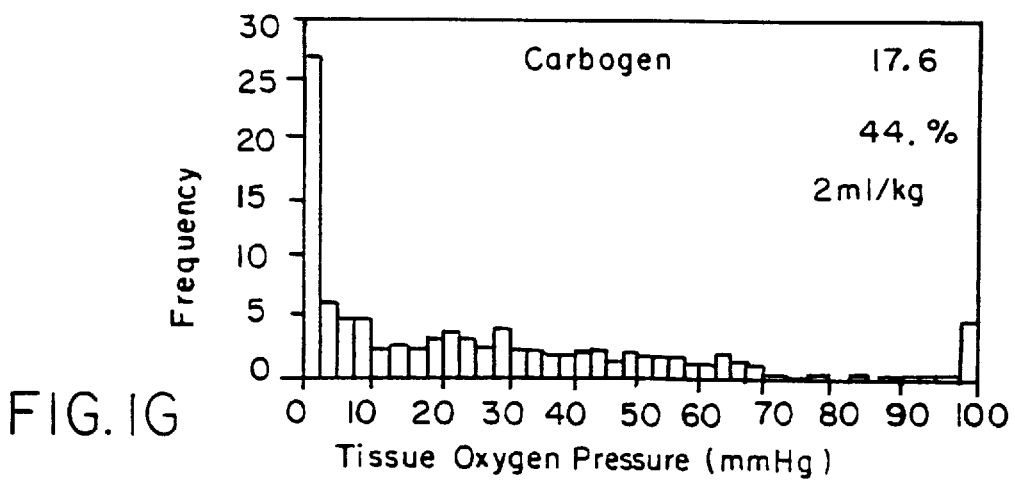
Figure 1H:
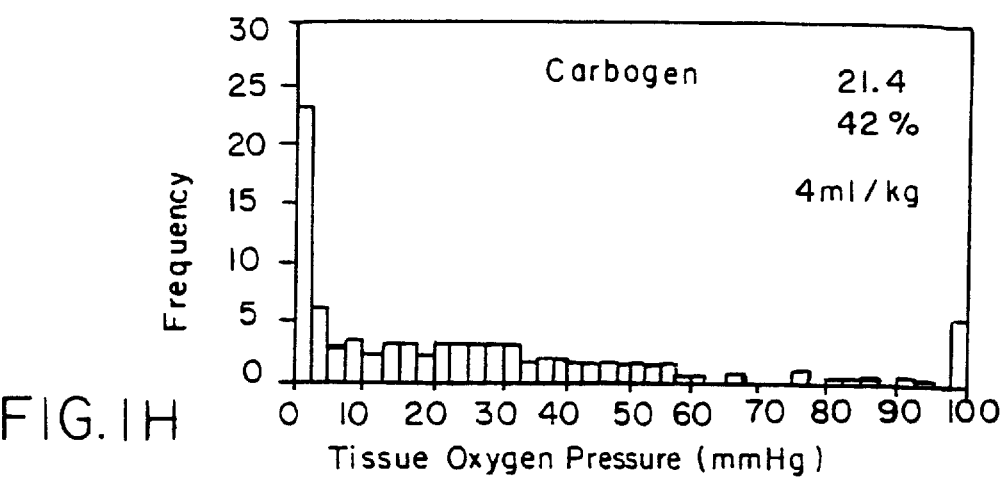
Figure 1I:
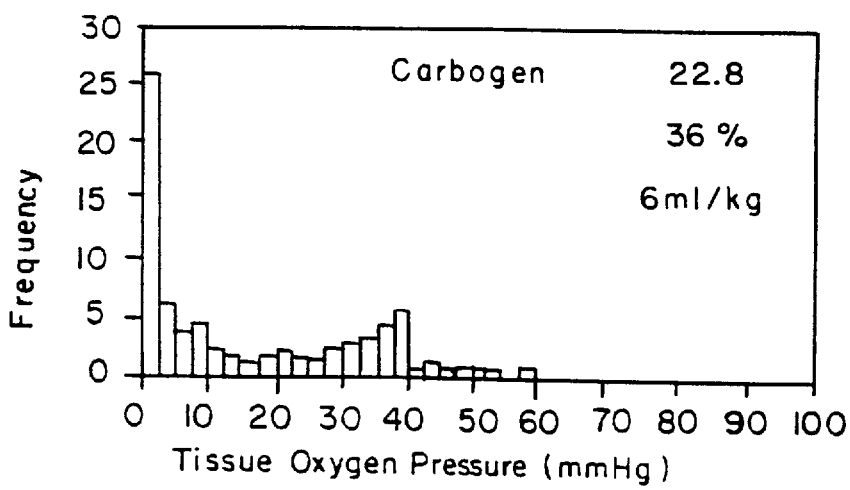
Figure 1J:
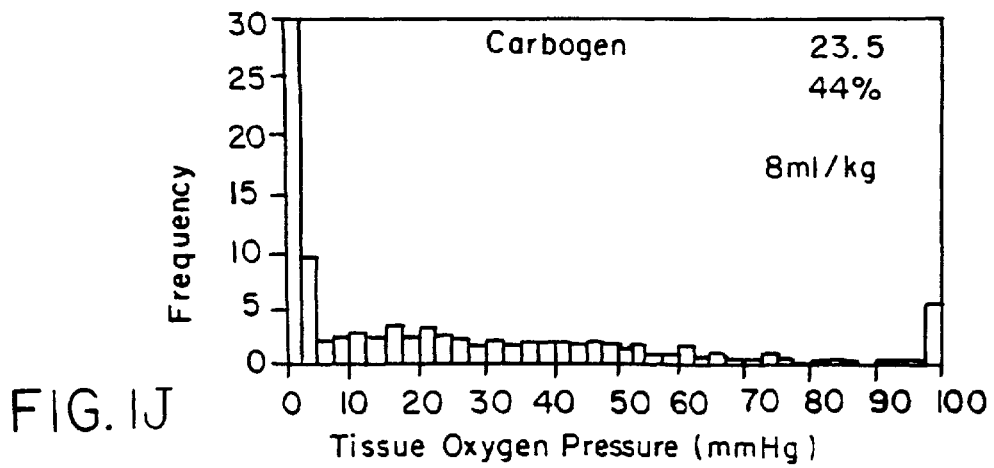

The present invention relates to a method of increasing effectiveness of oxygen delivery agents.

Oxygen delivery agents include hemoglobin-conjugates and also perfluorochemical emulsions.

The oxygen delivery agents can be used to enhance the effectiveness of certain anti-tumor therapies in animals such as mammals. These compounds are preferably used in conjunction with a therapy involving radiation, sometimes chemotherapies, or in combinations thereof. For example, it has been found that administering oxygen-delivery agents at a predetermined time for a sufficient period to rejuvenate the agent's effective life enhances the treatment. The predetermined time is selected based upon the time necessary to administer the oxygen-enriched atmosphere prior to administration of a treatment such as radiation to enhance the effectiveness of the treatment.

As used herein an oxygen enriched atmosphere has an $O_2$ content of 25% or more. Thus, one can obtain an effect with an oxygen-enriched atmosphere of at least about 25%, more preferably at 28%, still more preferably at least about 50%, even more preferably at least about 75% and most preferably at least about 95% $O_2$.

One preferred oxygen delivery agent whose effective life is increased by this method is a hemoglobin conjugate, such as poly(alkylene oxide)-conjugated hemoglobins. U.S. Pat. No. 5,478,806 discloses particularly preferred hemoglobin conjugate.

The conjugates include poly(alkylene oxide) modified hemoglobins. The poly(alkylene oxide) hemoglobin (PAO-Hb) conjugates are preferably administered in physiologically-acceptable solutions.

The conjugate is preferably formed by covalently bonding the hydroxyl terminals of the poly(alkylene oxide) and the free amino groups of lysine residues of the hemoglobin. See U.S. Pat. No. 5,234,903, which discloses PEG succinimidyl carbonate-Hb. Other art-recognized methods of conjugating the polymers with the Hb proteins, such as by via an amide or ester linkage, can also be used. Epsilon amino group modification of hemoglobin lysines is preferred. Covalent linkage by an atom between the hemoglobin and polymer is possible as well as non-covalent conjugation such as lipophilic or hydrophilic interactions.

Non-antigenic polymeric substances such as dextran, polyvinyl pyrrolidones, polysaccharides, starches, polyvinyl alcohols, polyacryl amides or other similar substantially non-immunogenic polymers can also be used.

The conjugate substituents are typically reacted under conditions which are appropriate to effect conjugation of the polymer and hemoglobin yet retain the ability of the hemoglobin or hemoglobin-like substance to transfer oxygen. The reactants are combined so that there is a several-fold molar excess of the polymeric substance over the hemoglobin. The reactions are carried out at temperatures of from about 0° to about 25° C. over time periods ranging from a few minutes to a few hours. The conjugate is purified using column chromatography or similar apparatus if necessary.

By controlling the molar excess of the polymer reacted with the hemoglobin the number of polymeric strands attached can be controlled. Preferable conjugates are taught as containing around 11 strands of PEG and can be made by reacting about a 15 to 20 fold molar excess of an activated PEG with hemoglobin.

The hemoglobin conjugates preferably have a molecular weight: of at least about 85,000 daltons and a degree of substitution of at least 5 poly(alkylene oxide) conjugates per hemoglobin molecule. More preferably, the conjugates have a molecular weight of at least 100,000 daltons and at least 8 poly(alkylene oxide) strands per hemoglobin conjugate, still more preferably at least 120,000 daltons and at least 11 poly(alkylene oxides) per hemoglobin molecule.

Polyethylene glycol (PEG) as the poly(alkylene oxide) is preferred. The poly(alklene oxides) include monomethoxy-polyethylene glycol, polypropylene glycol, block copolymers of polyethylene glycol and polypropylene glycol and the like. The polymers can also be distally capped with $C_{1-4}$ alkyls instead of monomethoxy groups.

The poly(alkylene oxides) used must be soluble in water at room temperature. Poly(alkylene oxides) having a molecular weight from about 200 to about 20,000 daltons are preferable, more preferably about 2,000 to about 10,000 and still more preferably about 5,000.

The hemoglobin (Hb) portion of the conjugates can be obtained from any appropriate mammalian source, human or non-human. Preferred non-human hemoglobins include bovine, fish ovine, porcine, birds, whales, sea lions, reptiles as well as others which can readily be obtained by the skilled artisan. Human hemoglobin can be obtained from whole human blood which has either been freshly drawn of obtained from "out-dated" supplies from blood banks. Human hemoglobin can also be obtained from placentas or packed erythrocytes obtained from blood donor centers. The hemoglobin can also be obtained from recombinant methods including the establishment of transgenic herds or cells. Such transgenic animals express wild type human, variant human or mutated human hemoglobins, for example. Non-human hemoglobins include ruminant hemoglobins, such as bovine and/or ovine sources. Porcine hemoglobins are also of use. Mammalian-species, specific hemoglobins are also contemplated. Fish hemoglobins can also be used. Pharmaceutically-acceptable solutions containing mixtures of various types of Hb conjugated to the poly(alkylene oxides) are also possible. The hemoglobin portion can account for about 20–80 percent of the weight of the conjugates.

The amount of conjugates contained in the solution can be in a range of about 0.2–40 wt %; solutions containing about 2–20 are preferred and solutions containing about 5–10 wt % are most preferred.

It was disclosed in U.S. Pat. No. 5,478,806 that such solutions were capable of delivering conjugates having an in vivo half-life of at least 2 hours, preferably, at least 6–18 hours and most preferably at least 12–20 hours in mammals. While it stated that preparations having in vivo half-lives of about 40–60 hours in mammals were also contemplated it did not describe how such a half-life was obtained.

The conjugate is administered in an amount which enhances antitumor therapy. Evidence of enhancement can be deduced by observation or by analytical measurements of increased local muscle/tissue/organ oxygen levels using apparatus designed for such purpose. One such apparatus is an OxySpot/OxyMap available from Medical Systems of Greenvale, N.Y. The maximum dose is the highest dosage that does not cause clinically important side effects. The conjugates can be administered directly into the bloodstream such via intravenous infusion or transfusion. In the case of transfusional therapy, the solutions can be administered in amounts ranging up to 70% of the patient's blood volume.

The hemoglobin conjugates were taught as typically being administered about 2 to 4 hours or less before each radiation dose. Typically, such conjugates were taught as being administered in amounts ranging from 0.24–6.3 g/kg and preferably in amounts ranging from 0.72–2.0 g/kg.

However, while coupling the hemoglobin with a conjugate such as PEG decreases immunogenicity and antigenicity of proteins, it cannot and does not remove this problem entirely. Thus, increasing the effective circulating life is important.

We have now found that by providing a subject that has received an oxygen delivery agent with an enriched oxygen atmosphere one can restimulate the oxygen delivery agent. Preferably the oxygen delivery agent has a circulatory half-life of at least about twelve hours, more preferably at least about fifteen hours, and still more preferably at least about twenty hours. The oxygen enriched atmosphere is administered by standard means well known in the art including nasal prongs, re-breather masks, respirators, hoods, etc. For example, we have shown that using 28% $O_2$ as shortly as 15 minutes before and during administration of radiation resulted in measurable decreases in the hypoxic fraction of the tumor as long as 3 days after the initial administration of the oxygen delivery agent. The oxygen delivery agent used had a circulating half-life of about 20 hours. Thus, the use of the present method can more than double the effective life, preferably increase it about three times, still more preferably increase the effective life at least about four times. While the use of $O_2$ enriched atmosphere of 25% or more provides a significant increase in effective life, further enhancements are obtained by using higher levels of oxygen. Preferred levels are at least 28% $O_2$, more preferably at least 50% $O_2$, still more preferably at least 75% $O_2$ and even more preferably at least about 95% $O_2$.

The time sufficient for extending the effective life by administration of the enriched oxygen atmosphere to the subject can begin as short as at least about 10 minutes before, more preferably 15 minutes before and during administration of the treatment, e.g. radiation or the chemotherapy. For example, with normal atmosphere, the hypoxic area immediately after administration of the hemoglobin-PEG conjugate was 55% decreasing at 24 hours to 46% then increasing at 98 hours to 53% with another slight decrease to 51% at 72 hours. In contrast, the hypoxic fraction decreased over 72 hours with an enriched oxygen rate as low as 28% $O_2$ was 30% at 72 hours. Similarly, the median $pO_2$ of the tumor increased from 8.1 mmHg to 26.0 mmHg in contrast. to that observed in normal air, which started at 3.8 initially and rose to 8.9 mmHg at 24 hours, thereafter decreasing.

Increasing oxygen levels higher than 28% resulted in continuing enhancement. For example, using carbogen, which contains 95% $O_2$, resulted in a starting hypoxic area of 36% which gradually decreased over 48 hours to 24% and at 72 hours decreased to 19%. The oxygen pressure almost doubled at the end of 48 hours and was 48.3 mmHg at the end of 72 hours.

Thus, whereas the effective life of the carrier in normal oxygen had peaked at about 24 hours, decreasing thereafter, it continued to increase when an oxygen enriched atmosphere was used. The results showed effective life through the entire time period test, which is 72 hours.

Accordingly, by using an oxygen enriched atmosphere as described herein, one can increase the effectiveness of these $O_2$ delivery agents and reduce the number of administrations. Thus, instead of needing to re-administer the oxygen delivery agent, such as the hemoglobin conjugate, if a day has passed since the previous administration, one does not have to re-administer the agent for at least 72 hours, more preferably, 96 hours. This reduces the treatment requirements.

Our results further show that the use of these enriched atmospheres can enhance the effectiveness of the radiation therapy. For example, tumor growth delay studies were carried on mice bearing the EMT-6 mammary carcinoma with fractionated radiation. The result in radiation dose modifying factors were 1.2 when the animal received air as opposed to 1.45 when the animal was exposed to 28% oxygen for 1 hour prior to and during radiation delivery vs. 1.70 when the animal received carbogen for that one hour. Thus, by the addition of enhanced oxygen, one can increase the effectiveness of these agents and also the effective circulating half-life.

As disclosed therein, the present invention is further illustrated by the following examples. These examples are provided as an aid to understanding the invention, and are not to be construed as a limitation thereof.

Materials and Methods Drugs.

PEG-Hemoglobin was prepared by coupling PEG (molecular weight 5000) through a succinimidyl carbonate linker to the $\epsilon$-amino groups of lysine resulting in a product with a molecular weight range of 120,000–130,000. PEG-Hemoglobin was prepared in a bicarbonate buffer with a protein concentration of 6 grams per deciliter. The $P_{50}$ of PEG-hemoglobin was 14 mmHg.

Tumors. Rat mammary adenocarcinoma 13672 is a carcinogen induced (DMBA) tumor of the female Fischer 344 rat. The tumor can metastasize to the lungs and abdominal organs. The tumor is composed of epithelial tissue in folds and acini. The tumor grows to 100 $mm^3$ in about 14 days when implanted subcutaneously (sc) in the hind legs of female rats [Teicher, B. A., et al., *Drugs Development Res.* 34:231–240 (1995)]. The EMT-6 murine mammary carcinoma is an in vivo-in vitro tumor system [Teicher, B. A., et al., *Semin. Oncol.* 17 (1[suppl. 3]):18–32:(1990)]. The EMT-6 tumor was carried in Balb/C mice (Taconic Farms, Germantown, N.Y.). For the experiments, $2 \times 10^6$ tumor cells prepared from a brief of several stock tumors were implanted intramuscularly into the legs of Balb/C mice 8 to 10 weeks old.

Oxygen Measurements Tissue oxygen measurements were made using a $pO_2$-Histograph (Eppendorf, Inc., Hamburg, Germany). The polarographic needle microelectrode was calibrated in aqueous solutions saturated with air or 100% nitrogen. The electrode was used in tumor measurements if there was less than 0.16% variation in current measurements upon repetition of the calibration cycle. For tumor $pO_2$ measurements, the animal was anesthetized by an intraperitoneal injection of Ketaset (35 mg/kg) and xylazine (25 mg/kg) prepared in phosphate-buffered 0.9% saline. The animal was placed on a heating pad and covered with a blanket to maintain body temperature. Core temperature was measured with a rectal thermometer. The tumor site was shaved and tumor diameters measured with calipers. A small patch of skin about 2 cm from tumor was shaved and a small incision was made allowing the reference electrode (Ag/AgCl-ECG) to be inserted sc and secured. The tumor was exposed by removing about 0.5 $cm^2$ of skin over the site. The tumor capsule was perforated with a 20-gauge needle. The $pO_2$ microelectrode was positioned in the perforation.

The $pO_2$ microelectrode under computer control enters 1 mm into the tissue and then retracts 0.3 mm. Probe current is then measured and after 1.4 seconds the probe moves forward again. The total length of the measurement path is determined by the size of the tumor. After the probe reaches the end of its measurement path, it automatically retracts. The probe was then repositioned in the same perforation at a different angle and stepwise measurements again initiated. Three diameters were measured in each tumor for a total of 50–60 measurements per condition.

Tumor $pO_2$ measurements were made under several conditions: (1) normal air breathing, (2) 28% oxygen breathing, (3) carbogen (95% $O_2$/5% $CO_2$) breathing, (4) PEG-Hb (2, 4, 6 and 8 ml/kg) intravenous administration with normal air breathing, (5) PEG-Hb (2, 4, 6 and 8 ml/kg) intravenous administration with carbogen breathing, and (6) PEG-Hb (6 ml/kg) intravenous with 28% oxygen breathing. Oxygen measurements were made 10 minutes, 3 hours, 24 hours, 48 hours and 72 hours after PEG-Hb administration. Data collection through three tumor diameters accrued about 50 $pO_2$ measurements and took about 10 minutes. The $pO_2$ microelectrode was recalibrated in aqueous solutions saturated with air and 100% nitrogen after each data collection; therefore, the $pO_2$ microelectrode was recalibrated 4 times during the course of the experiments. Recalibration requires about 15 minutes [Teicher, B. A. et al., *Drug Development Res.* 34:231–240 (1995)].

Serum PEG-Hemoglobin Serum PEG-Hemoglobin levels were determined using Sigma Plasma Hemoglobin Kit #527A (Sigma Chemical Co., St. Louis, Mo.). Blood was collected over time from the ocular sinus and serum prepared from rats bearing the 13762 mammary carcinoma that had received PEG-hemoglobin (0 or 6 ml/kg) by intravenous injection. The measurements are expressed as grams PEG-hemoglobin per deciliter serum.

Rat 13762 Tumor Growth Delay Rat 13762 mammary carcinoma cells ($2\times10^6$) prepared from brief of stock tumors were implanted subcutaneously into a hind leg of Fischer 344 female rats. Fractionated radiation therapy (2, 3, and 4 Gray per fraction daily for 5 days) was delivered locally to the tumor-bearing limb (0.9 Gray/min; Gamma Cell 40, Atomic Energy of Canada, Ltd., Ottawa, Ontario) beginning when the subcutaneous tumors reached 100 mm$^3$ in volume (14 days post tumor cell implantation). The shielded portion of the animal received less than 2% of the delivered radiation dose.

PEG-Hb (8 ml/kg) was administered intravenously 1 hour prior to each radiation fraction. Breathing of air, 28% oxygen or carbogen was maintained for 1 hour prior to and during radiation delivery.

The progress of each subcutaneous tumor was measured 3 times/week until it reached a volume of 2,000 mm$^3$. Tumor growth delay was calculated as the number of days for each individual tumor to reach 500 mm$^3$ compared with the untreated controls. Each treatment group had 4 animals and the experiment was repeated twice. Days of tumor growth delay are the mean ± S.E.M for the treatment group compared with the control [Teicher, B. A., et al., *Drug Development Res.* 34:231–240 (1995)]; Teicher, B. A., et al., *Semin. Oncol.* 17 (1[suppl. 3]):18–32:(1990)].

Tumor Cell Survival When the EMT-6 murine mammary carcinoma tumors were approximately 100 mm$^3$ in volume (about 1 week after tumor cell implantation), PEG-Hb (8 or 6 ml/kg) was administered intravenously. The animals were then allowed to breathe air, 28% oxygen or carbogen for 1 hour prior to and during delivery treatment to allow for full expression of drug cytotoxicity and repair of potentially lethal damage and then soaked in 95% ethanol. The tumors were excised, and single cell suspensions were prepared [Teicher, B. A., et al., *Semin. Oncol.* 17 (1[suppl. 3]):18–32: (1990); Teicher, B. A., et al., *Cancer Res.* 47:513–518 (1987)]. The untreated tumor cell suspensions had a plating efficiency of 8% to 12%. The results are expressed as the surviving fraction ± S.E.M. of cells from treated groups compared with untreated controls.

Murine EMT-6 Tumor Growth Delay When the EMT-6 tumors were approximately 100 mm$^3$ in volume (day 7 after tumor cell implantation), PEG-Hb (6 ml/kg) was administered intravenously daily or on treatment day 1 only, and the animals were then allowed to breathe air, 28% oxygen or carbogen for 1 hour prior to and during radiation delivery. Radiation was delivered locally to the tumor-bearing limb (0.9 Gray/min; Gamma Cell 40, Atomic Energy of Canada, Ltd., Ottawa, ON).

The progress of each tumor was measured three times weekly until the tumor reached a volume of 500 mm$^3$. Tumor growth delay was calculated as the days taken by each individual tumor to reach 500 mm$^3$ compared with the untreated controls. Tumor volume was calculated as a hemiellipsoid. Untreated EMT-6 tumors reached 500 mm$^3$ in 12.2±0.4 days. Each treatment group had five animals, and the experiment was repeated three times. Days of tumor growth delay are the means ± S.E.M. for the treatment group compared with the controls [Teicher, B. A., et al., *Semin. Oncol.* 17 (1[suppl. 3]):18–32:(1990); Teicher, B. A., et al., *Cancer Res.* 47:513–518 (1987)].

Results

A computerized polarographic pO$_2$ microelectrode was used to measure the oxygen tension in the rat 13762 mammary carcinoma after intravenous administration of various doses of PEG-Hb to animals breathing air or carbogen (95% oxygen/5% carbon dioxide) (FIG. 1). In the untreated tumors under normal air breathing conditions, the median pO$_2$ was 3.2 mmHg and the hypoxic fraction (the percent of pO$_2$ readings$\leq$5 mmHg) was 65%. Administration of PEG-Hb over the dosage range from 2 ml/kg to 8 ml/kg decreased the hypoxic fraction of the tumor 7 to 18%. Carbogen breathing saturates the plasma with oxygen. When carbogen breathing was maintained for 15 minutes prior to and during the oxygen measurement, the median pO$_2$ in the tumors was 17.7 mmHg and the hypoxic fraction was 49%. Upon administration of PEG-Hb (6 ml/kg) the hypoxic fraction of the tumor was decreased to 36%.

Figure 2:
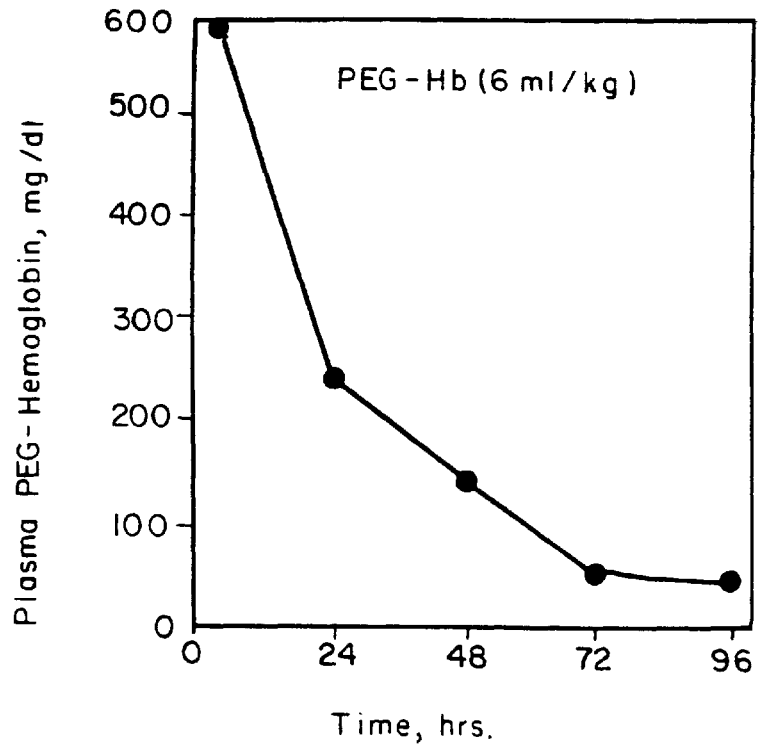
FIG. 2 are plasma PEG-hemoglobin levels over time after intravenous administration of PEG-hemoglobin (6 ml/kg) on day 0. Data are the means; bars are the S.E.M.
Figure 3A:
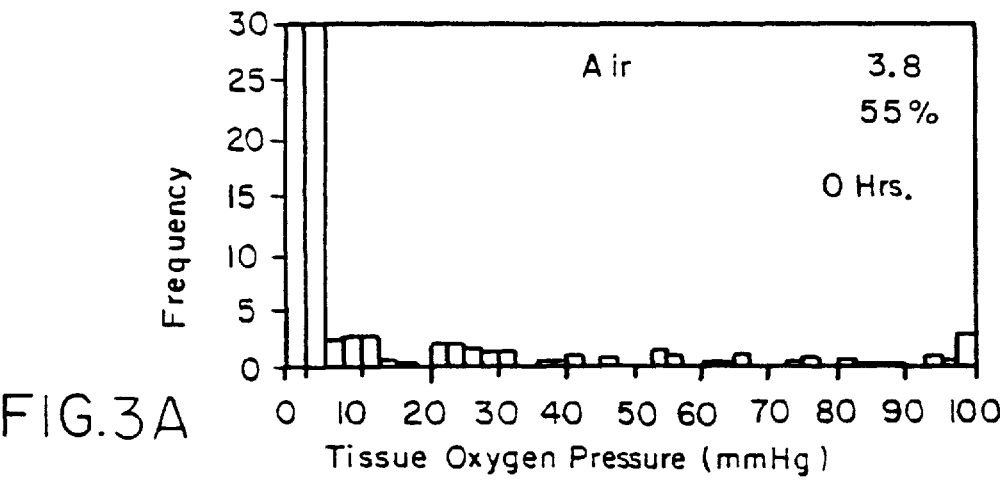
FIGS. 3A–O are histograms showing the oxygen profiles as well as the median $pO_2$ values (top number in each histogram, in mmHg) and the percent of $pO_2$ values $\leq 5$ mmHg (bottom number in each histogram) for the rat 13672 mammary carcinoma under normal air breathing (FIGS. 3A–3E), 28% oxygen (FIGS. 3F–J) and carbogen (95% oxygen/5% carbon dioxide) (FIGS. 3K–3O) breathing conditions alone (FIGS. 3A, 3F, 3K), or after intravenous administration of the PEG-Hb (6 ml/kg). Measurements of $pO_2$ were made 10 min, 3 hours (FIGS. 3B, 3G, 3L) 6 hours, 24 hours (FIGS. 3C, 3H, 3M), 48 hours (FIGS. 3D, 3I, 3N), and 72 hours (FIGS. 3E, 3J, 3O) after intravenous administration of the PEG-Hb. Approximately 50 measured values were obtained per tumor per condition. Each histogram represents 500–3,000 measured $pO_2$ values.
Figure 3B:
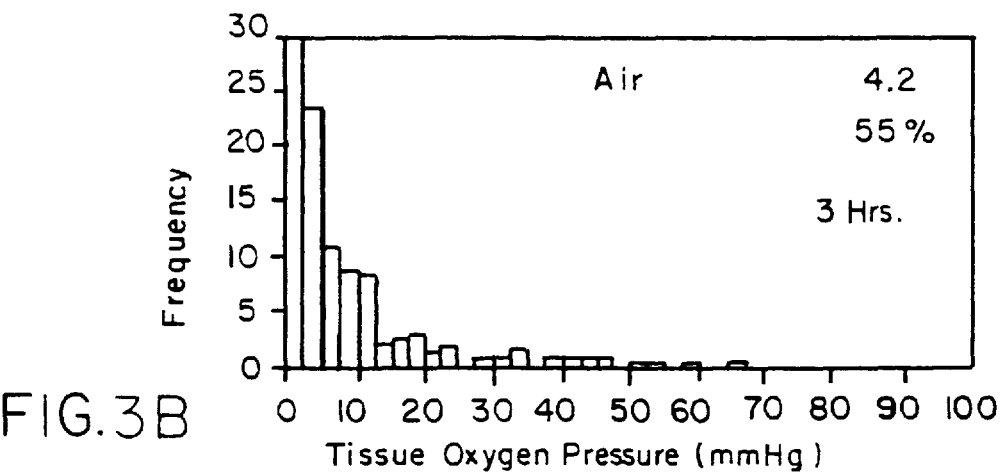
Figure 3C:
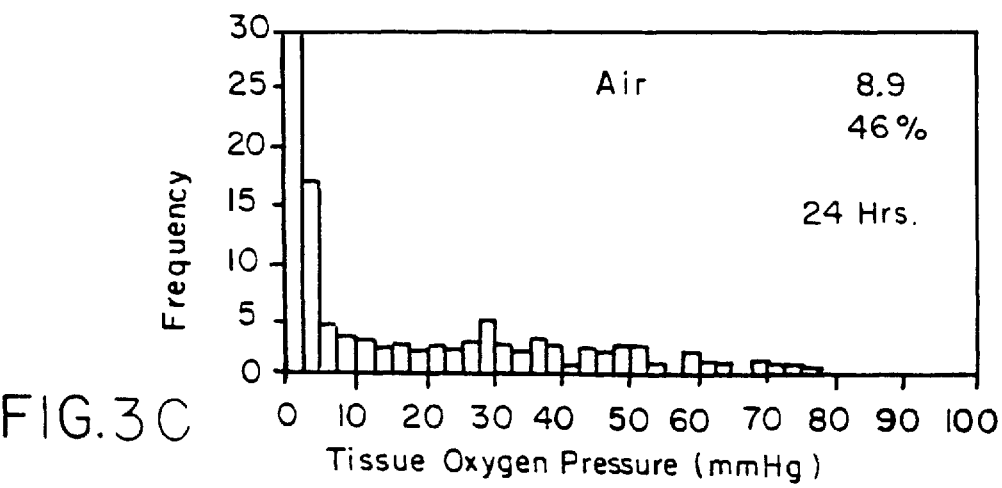
Figure 3D:
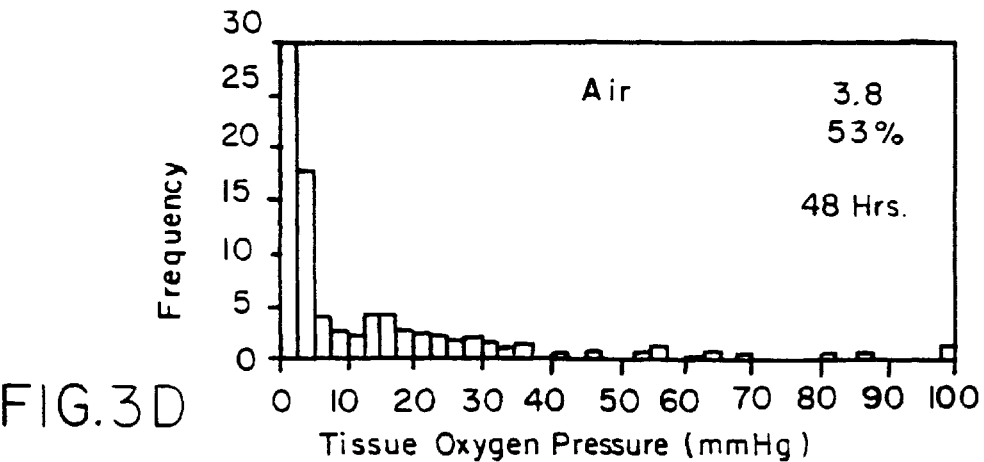
Figure 3E:
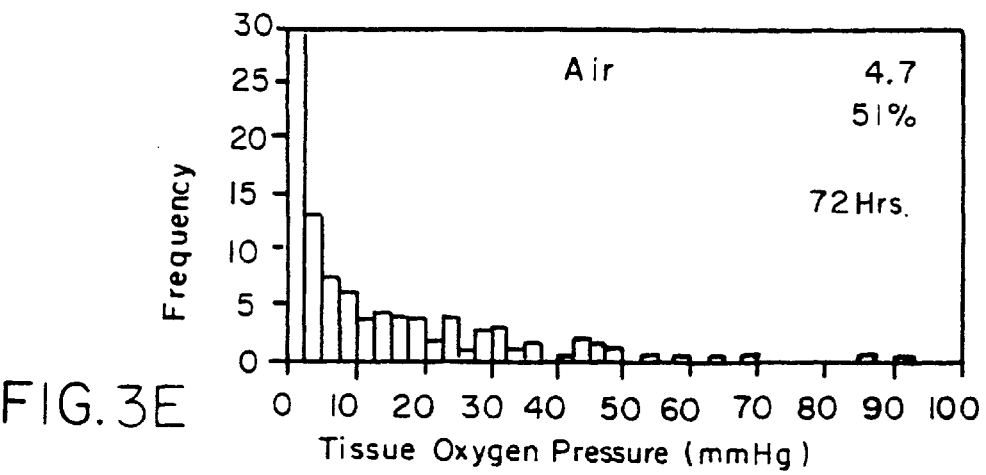
Figure 3F:
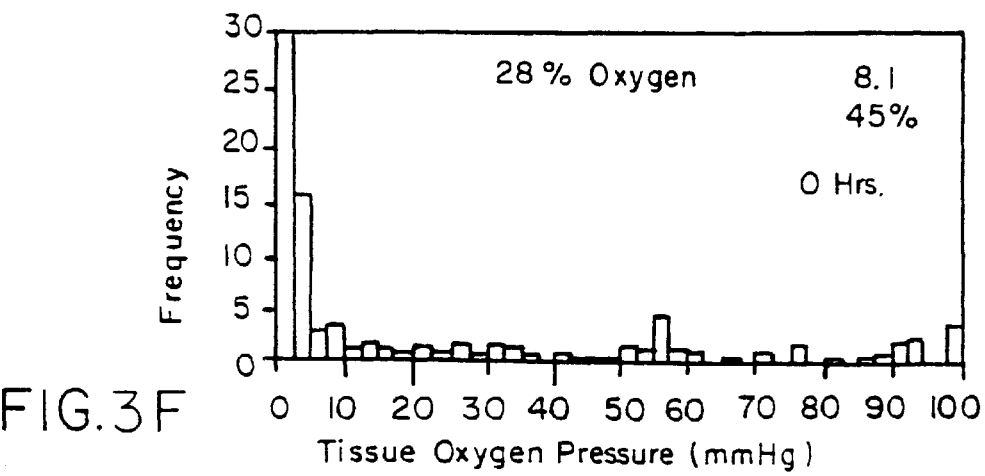
Figure 3G:
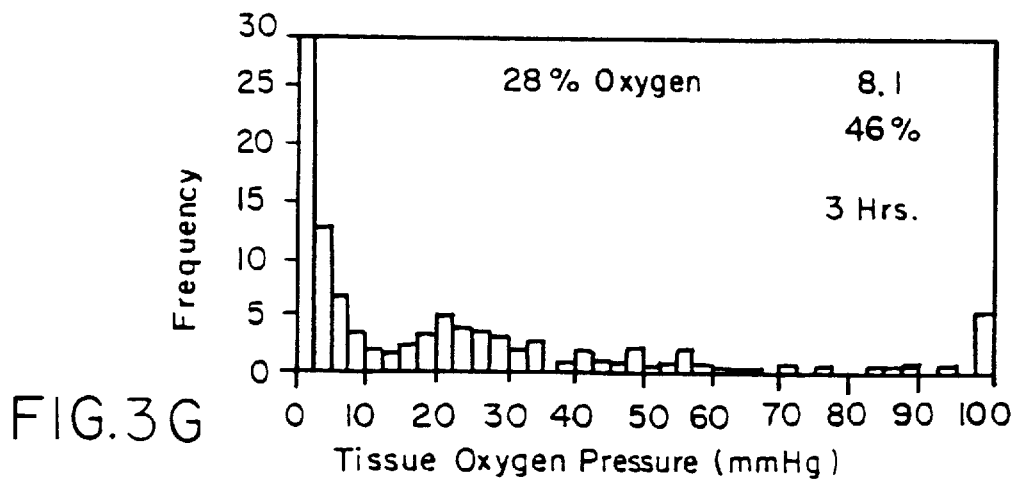
Figure 3H:
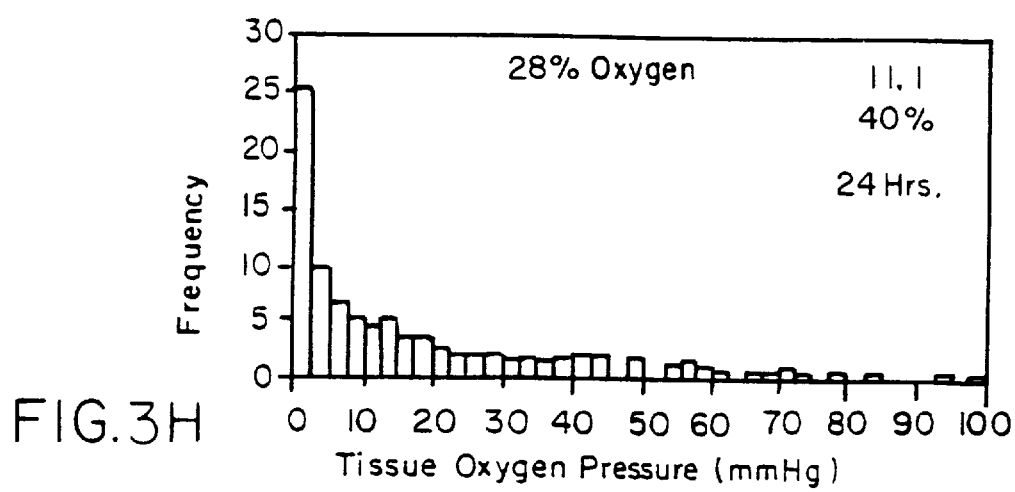
Figure 3I:
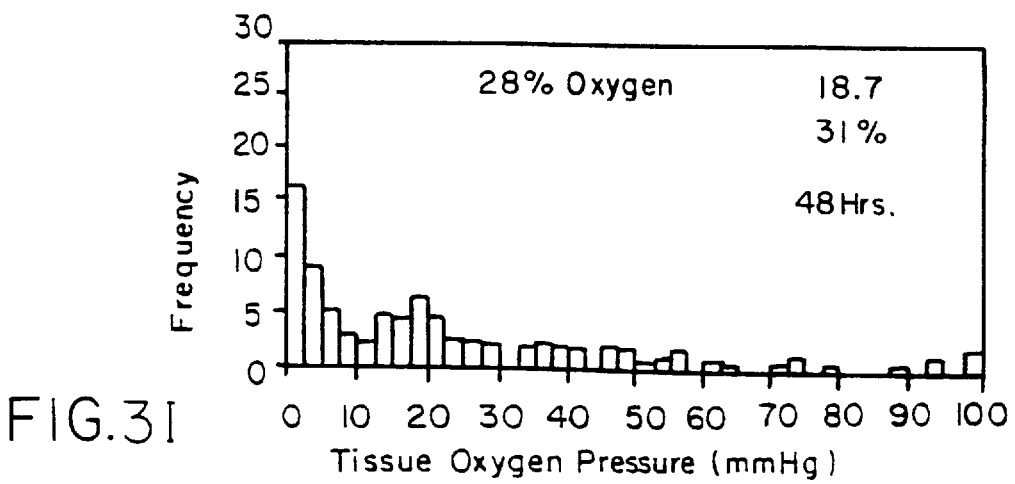
Figure 3J:
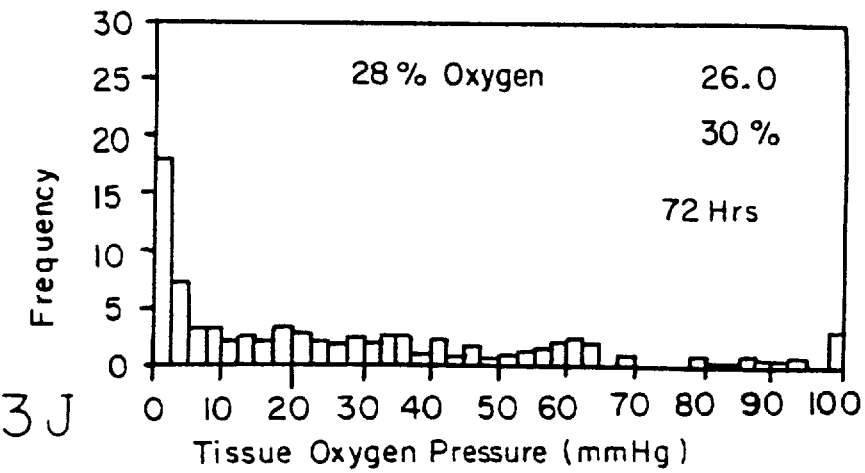
Figure 3K:
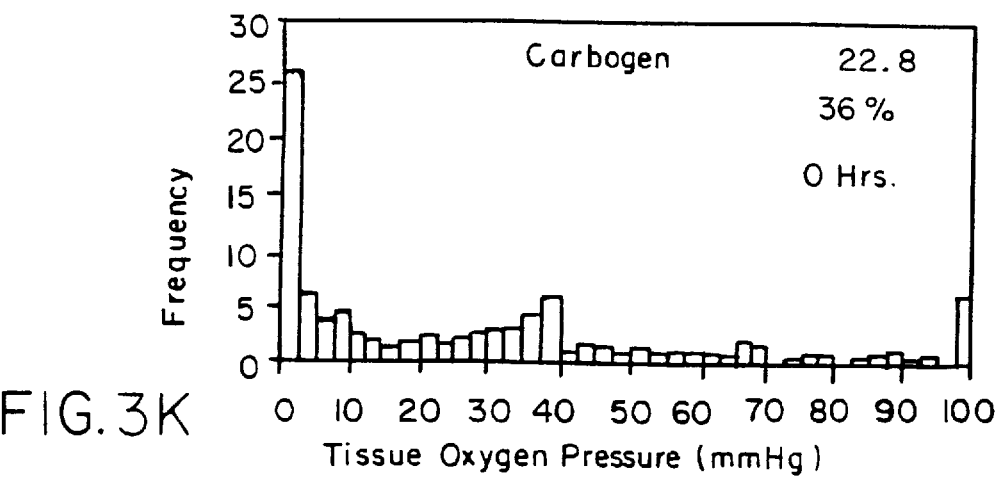
Figure 3L:
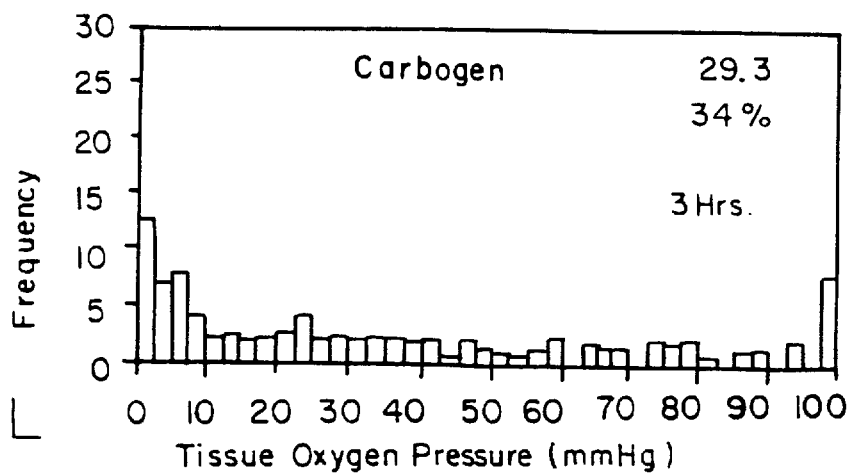
Figure 3M:
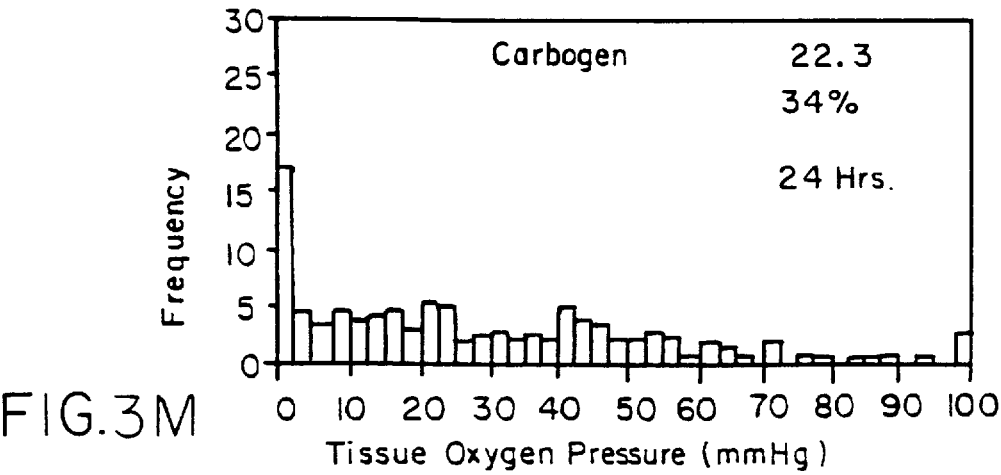
Figure 3N:
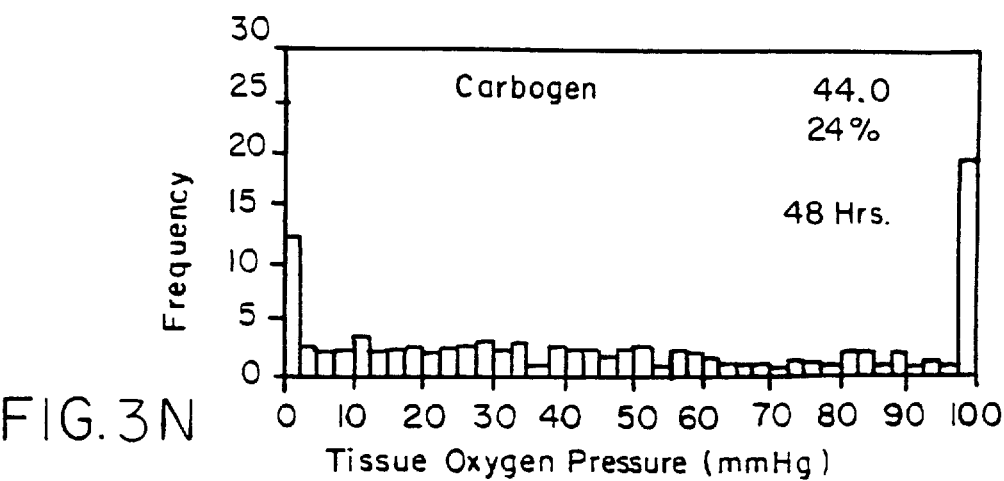
Figure 3O:
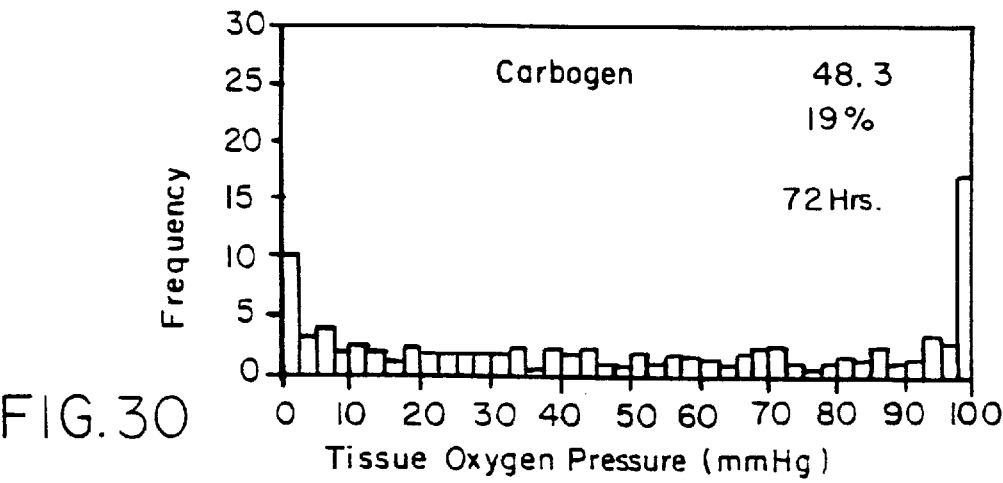

PEG-Hb has a circulating half-life of about 20 hours in rats bearing the 13762 mammary carcinoma after intravenous administration of a dose of 6 ml/kg (FIG. 2). To mimic a potential clinical regimen of PEG-Hb administration once or twice per week, PEG-Hb (6 ml/kg, iv) and tumor oxygenation measurements were made under three breathing conditions over a 3 day period (FIG. 3). Increasing the inhaled oxygen content from 20% to 28% resulted in a measurable decrease in the hypoxic fraction of the tumor that was intermediate between the hypoxic fraction observed with air breathing and the hypoxic fraction observed with carbogen breathing. Over the 3-day time course examined, there were no marked changes in tumor oxygenation in the animals breathing air. However, when the animals breathed 28% oxygen or carbogen there was a trend toward increased responsiveness of the tumors to oxygen delivery as indicated by increasing median pO$_2$'s and decreased hypoxic fractions. Over the time course, the median pO$_2$ of the tumor increased from 8.1 mmHg to 26.0 mmHg and the hypoxic fraction decreased from 45% to 30% when the animals breathed 28% oxygen for 15 minutes prior to and during oxygen measurements. Similarly, over the time course, the median pO$_2$ of the tumor increased from 22.8 mmHg to 48.3 mmHg and the hypoxic fraction decreased from 36% to 19% when the animals breathed carbogen for 15 minutes prior to and during the oxygen measurements.

The rat 13762 mammary carcinoma is a moderately radiosensitive tumor. To mimic one week of a clinical regimen, radiation therapy was administered locally to the tumor-bearing limb in fractions of 2, 3 or 4 Gray daily for 5 days (Table 1). The radiation treatment resulted in increasing tumor growth delay with increasing total dose of radiation. The administration of PEG-Hb 1 hour prior to each radiation fraction improved the response of the tumor to radiation therapy so that the radiation dose modifying factors were 1.20, 1.35 and 1.50 when the animals breathed air, breathed 28% oxygen or breathed carbogen, respectively.

TABLE 1

Growth delay of the 13762 rat mammary carcinoma produced by fractionated radiation therapy with or without daily administration of PEG-Hb.

| TREATMENT GROUP | TUMOR GROWTH DELAY, DAYS[a] + PEG-Hb (8 ml/kg) | | | |
|---|---|---|---|---|
| | ALONE | AIR | 28% $O_2$ | 95% $O_2$ |
| 5 × 2 Gray | 2.0 ± 0.4 | 2.7 ± 0.4 | 4.7 ± 0.5 | 6.2 ± 0.6 |
| 5 × 3 Gray | 5.4 ± 0.7 | 6.4 ± 0.6 | 6.9 ± 0.7 | 8.3 ± 0.8 |
| 5 × 4 Gray | 7.2 ± 1.1 | 9.6 ± 1.2 | 9.9 ± 1.2 | 11.6 ± 1.3 |
| Dose Modifying Factor[b] | — | 1.20 | 1.35 | 1.50 |

[a]Mean days ± S.E.M. for treated tumors to reach 500 mm$^3$ compared with untreated controls. Control tumors reached 500 mm$^3$ in 17.5 ± 1.2 days. Radiation therapy was delivered locally to the tumor-bearing limb as fractions on days 7–11 using $^{137}$Cs gamma rays (dose rate, 0.88 Gy/min). Animals were irradiated unanesthetized. Carbogen breathing or 28% oxygen atmosphere breathing was maintained for 1 hour prior to and during radiation therapy delivery. Each treatment group has 4 animals and the experiment was repeated 3-times, therefore the number of animals per point was 12 (n = 12).
[b]The radiation dose modifying factor was calculated as the ratio of the days for the radiation-alone treatment group compared with the PEG-Hb treated group to reach 6 days of tumor growth delay.

Figure 4:
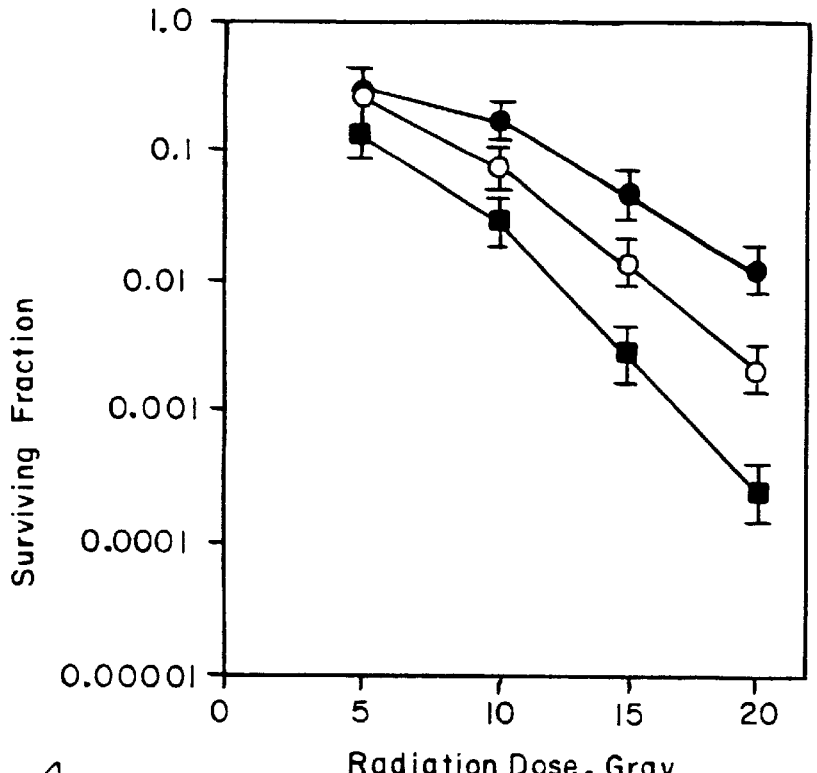
FIG. 4 shows survival of EMT-6 tumor cells from tumors treated in vivo with single does radiation (●), Peg-Hb (8 ml/kg, iv) (□), PEG-Hb (8 ml/kg, iv) 1 hours prior to irradiation (○) or PEG-Hb (8 ml/kg,iv) and carbogen breathing 1 hour prior to and during irradiation (■). Results are presented as the means of three independent determinations; bars are S.E.M.
Figure 5:
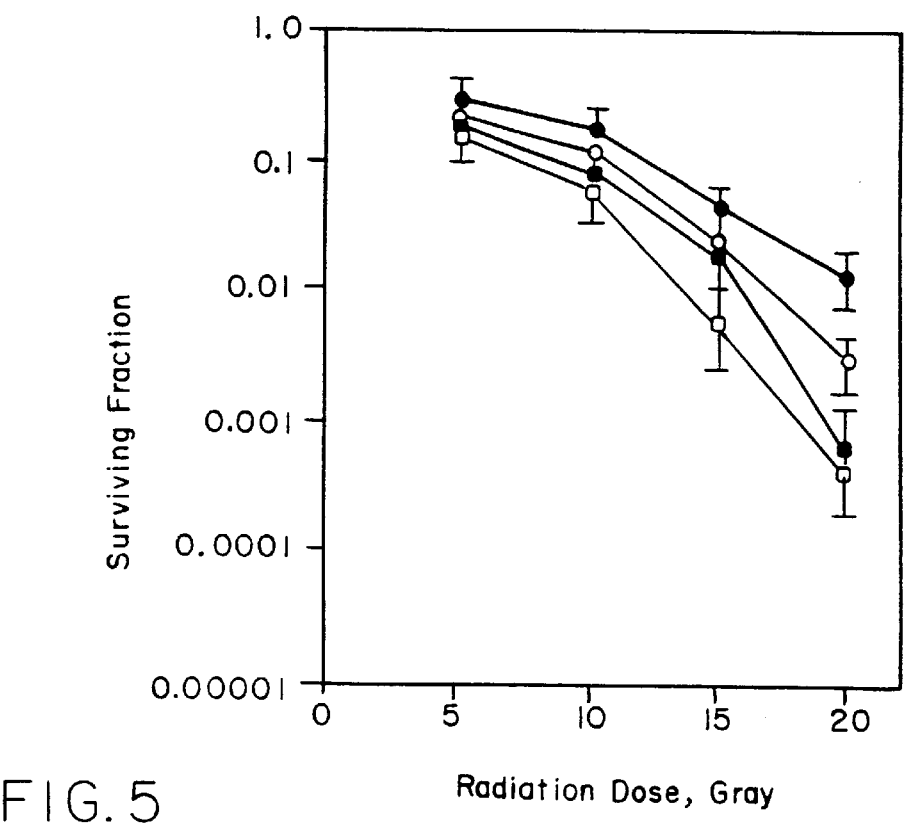
FIG. 5 shows survival of EMT-6 tumor cells from tumors treated in vivo with single does radiation (●), PEG-Hb (6 ml/kg, iv) (Δ), PEG-Hb (6 ml/kg, iv) 1 hour prior to irradiation (○), PEG-Hb (6 ml/kg, iv) and 28% oxygen breathing 1 hour prior to and during irradiation (■) or PEG-Hb (6 ml/kg, iv) and carbogen breathing 1 hour prior to and during irradiation (□). Results are presented as the means of three independent determinations; bars are S.E.M.

To analyze the efficacy of PEG-Hb administration as a radiation sensitizes in a second tumor system, tumor cell survival was assayed from animals bearing the murine EMT-6 mammary carcinoma (FIG. 4). The tumor bearing animals were treated with single dose radiation alone or 1 hour after intravenous administration of PEG-Hb (8 ml/kg) and air or carbogen breathing during radiation delivery. Administration of PEG-Hb had a dose modifying effect on the response of the tumor cells to radiation. The PEG-Hb dose modifying factor when the animals breathed air was 1.50 and when the animals breathed carbogen was 2.00. Using the same single dose radiation treatment with prior intravenous administration of PEG-Hb (6 ml/kg) and air breathing, 28% oxygen breathing or carbogen breathing prior to and during radiation delivery resulted in radiation dose modifying factors of 1.40, 1.80, and 1.90 (FIG. 5).

Tumor growth delay studies were carried out in mice bearing the EMT-6 mammary carcinoma with fractionated radiation (Table 2). Intravenous administration of PEG-Hb (6 ml/kg) 1 hour prior to radiation increased the tumor growth delay at each radiation therapy dose level. The resulting radiation dose modifying factors were 1.20, 1.45 and 1.70 when the animals breathed air, when the animals breathed 28% oxygen and when the animals breathed carbogen for 1 hour prior to and during radiation delivery, respectively.

TABLE 2

Growth delay of the murine EMT-6 mammary carcinoma produced by fractionated radiation therapy with or without daily administration of PEG-Hb.

| TREATMENT GROUP | TUMOR GROWTH DELAY, DAYS[a] + PEG-Hb (6 ml/kg) | | | |
|---|---|---|---|---|
| | ALONE | AIR | 28% $O_2$ | 95% $O_2$ |
| 5 × 2 Gray | 1.6 ± 0.3 | 2.8 ± 0.4 | 3.6 ± 0.3 | 4.9 ± 0.4 |
| 5 × 3 Gray | 4.3 ± 0.4 | 5.3 ± 0.5 | 6.2 ± 0.6 | 8.7 ± 0.6 |
| 5 × 4 Gray | 6.2 ± 0.4 | 7.1 ± 0.6 | 10.4 ± 0.9 | 13.1 ± 0.9 |
| Dose Modifying Factor[b] | — | 1.20 | 1.45 | 1.70 |

[a]Mean days ± S.E.M. for treated tumors to reach 500 mm$^3$ compared with untreated controls. Control tumors reached 500 mm$^3$ in 12.4 ± 1.2 days. Radiation therapy was delivered locally to the tumor-bearing limb as fractions on days 7–11 using $^{137}$Cs gamma rays (dose rate, 0.88 Gy/min). Animals were irradiated unanesthetized. Carbogen breathing or 28% oxygen atmosphere breathing was maintained for 1 hour prior to and during radiation therapy delivery. Each treatment group has 5 animals and the experiment was repeated 3-times, therefore the number of animals per point was 15 (n = 15).
[b]The radiation dose modifying factor was calculated as the ratio of the days for the radiation-alone treatment group compared with the PEG-Hb treated group to reach 6 days of tumor growth delay.

In the experiments shown in Table 3 the administration of PEG-Hb was limited to once on the first treatment day. Fractionated radiation therapy was delivered daily for 5 days with the animals breathing air, breathing 28% oxygen for 1 hour prior to and during radiation delivery or breathing carbogen for 1 hour prior to and during radiation delivery. Allowing the animals that did not receive the PEG-Hb to breathe atmospheres with increased oxygen levels did not increase the tumor response to radiation therapy. However, allowing animals previously treated with PEG-Hb to breathe atmospheres containing 28% or 95% oxygen for 1 hour prior and during each radiation fraction produced radiation dose modifying factors or 1.25 and 1.40, respectively.

TABLE 3

Growth delay of the murine EMT-6 mammary carcinoma produced by a fractionated regimen of 3 Gray daily for 5 days with or without administration of PEG-Hb on the first treatment day only.

| TREATMENT GROUP | TUMOR GROWTH DELAY, DAYS[a] + PEG-Hb (6 ml/kg) | |
|---|---|---|
| | ALONE | +PEG Hb (6 ml/kg) |
| Air/5 × 3 Gy | 4.3 ± 0.4 | 4.8 ± 0.4 |
| 28% $O_2$/5 × 3 Gy | 4.4 ± 0.4 | 5.5 ± 0.5 |
| 95% $O_2$/5 × 3 Gy | 4.4 ± 0.4 | 6.2 ± 0.6 |

[a]Mean days ± S.E.M. for treated tumors to reach 500 mm$^3$ compared with untreated controls. Control tumors reached 500 mm$^3$ in 12.4 ± 1.2 days. Radiation therapy was delivered locally to the tumor-bearing limb as fractions on days 7–11 using $^{137}$Cs gamma rays (dose rate, 0.88 Gy/min). Animals were irradiated unanesthetized. Carbogen breathing or 28% oxygen atmosphere breathing was maintained for 1 hour prior to and during radiation therapy delivery. Each treatment group has 5 animals and the experiment was repeated 3-times, therefore the number of animals per point was 15 (n = 15).

In the application of oxygen delivery agents to the clinic, practical issues such as lack of toxicity and circulating half-life will become very important factors. Derivatization of proteins with polyethylene glycol through a linker has proven to be a highly biocompatible method for decreasing the toxicity and increasing the circulating half-life of protein therapeutics [Abuchowski, A., et al., *Cancer Biochem. Biophys.* 7:175–185 (1984); Davis, F., et al., *Enyzme Eng.* 4:169–173 (1978); Davis, F. F., et al., Lee VHL, ed. *Peptide and Protein Drug Delivery*, NY; Marcel Dekker (1991); Davis, S., et al., *Clin. Exp. Immunol.* 46:649–652 (1981); Fuertges, F., et al., *J. Controlled Release* 11:139–148 (1990);

Hershfield, M. S., et al., *New. Eng. J. Med.* 310:589–596 (1987); Keating, M. J., et al., *Leuk. Lymphoma* 10, suppl:153–157 (1993); Nucci, J. L., et al., *Adv. Drug Deliv. Rev.* 6:133–151 (1991)]k. The amounts of hemoglobin that will be administered is relatively very high. The data presented here indicated that oxygen deliver agents such as PEG-Hb especially with breathing a high oxygen content atmosphere can decrease hypoxia in tumors in a therapeutically important manner and that the effective circulating half-life of the delivery agent can be enhanced (i.e. the efficacy of an oxygen delivery agent such as PEG-Hb can be "recalled") by breathing a $O_2$-enriched atmosphere even several days after of the agent administration.

It is evident that those skilled in the art given the benefit of the foregoing disclosure may make numerous modifications thereof, and departures from the specific embodiments described herein, without departing from the inventive concepts, and the present invention is to be limited solely to the scope and spirit of the appended claims.

What is claimed is:

1. A method of treating an animal in need of an antitumor therapy comprising administering an effective antitumor amount of a chemotherapy and/or radiation in conjunction with an effective amount of an oxygen-delivery agent, wherein said oxygen-delivery agent is a hemoglobin-polymer conjugate, wherein the effective life of the oxygen delivery agent is increased thereby decreasing the number of administrations of the oxygen-delivery agent by subjecting the animal to an oxygen-enriched atmosphere at a predetermined time for a sufficient period to at least double the effective life of the oxygen-delivery agent, wherein the effective life of the oxygen-delivery agent is determined under normal atmospheric conditions, wherein said hemoglobin-polymer conjugate is hemoglobin covalently conjugated to a poly(alkylene oxide).

2. The method of claim 1, wherein said poly(alkylene oxide) is a polyethylene glycol.

3. A method of treating an animal in need of an antitumor therapy comprising administering an effective antitumor amount of a chemotherapy and/or radiation in conjunction with an effective amount of an oxygen-delivery agent, wherein said oxygen-delivery agent is a hemoglobin polymer conjugate, wherein the effective life of the oxygen delivery agent is increased thereby decreasing the number of administrations of the oxygen-delivery agent by subjecting the animal to an oxygen-enriched atmosphere at a predetermined time for a sufficient period to at least double the effective life of the oxygen-delivery agent, wherein the effective life of the oxygen-delivery agent is determined under normal atmospheric conditions.

4. The method of claim 3, wherein the predetermined time is at least 10 minutes prior to administration of said therapy.

5. The method of claim 4 wherein said antitumor therapy is radiation and the oxygen-enriched atmosphere is administered beginning at least 10 minutes prior to said therapy and during said therapy.

6. The method of claim 4, wherein said oxygen-enriched atmosphere has an $O_2$ content of at least about 28%.

7. The method of claim 5, wherein said oxygen-enriched atmosphere has an $O_2$ content of at least about 28%.

8. The method of claim 4, wherein said oxygen-enriched atmosphere has an $O_2$ content of at least about 50%.

9. The method of claim 5, wherein said oxygen-enriched atmosphere has an $O_2$ content of at least about 50%.

10. The method of claim 4, wherein said oxygen-enriched atmosphere has an $O_2$ content of at least about 95%.

11. The method of claim 5, wherein said oxygen-enriched atmosphere has an $O_2$ content of at least about 95%.

12. The method of claim 3, wherein said oxygen-delivery agent has a circulatory half-life of at least about fifteen hours.

13. The method of claim 3, wherein hemoglobin-polymer conjugate has an effective life under an oxygen-enriched atmosphere of about 72 hours.

14. The method of claim 13, wherein said poly(alkylene oxide) is a polyethylene glycol.

* * * * *